United States Patent
Wang et al.

(10) Patent No.: US 9,744,492 B2
(45) Date of Patent: Aug. 29, 2017

(54) AIR PURIFIER

(71) Applicant: Beijing FUNATE Innovation Technology Co., LTD., Beijing (CN)

(72) Inventors: Yu-Quan Wang, Beijing (CN); Li Qian, Beijing (CN)

(73) Assignee: Beijing FUNATE Innovation Technology Co., LTD., Beijing (CN)

( * ) Notice: Subject to any disclaimer, the term of this patent is extended or adjusted under 35 U.S.C. 154(b) by 224 days.

(21) Appl. No.: 14/751,162

(22) Filed: Jun. 26, 2015

(65) Prior Publication Data

US 2016/0016105 A1    Jan. 21, 2016

(30) Foreign Application Priority Data

Jul. 16, 2014    (CN) .................... 2014 2 0392710 U

(51) Int. Cl.
*B01D 46/00* (2006.01)
*B01D 46/10* (2006.01)
*A61L 2/02* (2006.01)
*B01D 39/20* (2006.01)

(52) U.S. Cl.
CPC .............. *B01D 46/10* (2013.01); *A61L 2/022* (2013.01); *B01D 39/2065* (2013.01); *B01D 46/0028* (2013.01); *B01D 46/0036* (2013.01); *B01D 46/0032* (2013.01); *B01D 2239/1233* (2013.01)

(58) Field of Classification Search
CPC ............ B01D 39/2055; B01D 39/2065; B01D 2239/1216; B01D 46/10; A61L 2/022
See application file for complete search history.

(56) References Cited

U.S. PATENT DOCUMENTS

| | | | | |
|---|---|---|---|---|
| 7,045,108 B2* | 5/2006 | Jiang | ................ | B01J 23/74 423/447.1 |
| 7,993,589 B1* | 8/2011 | Shigemoto | ................ | A61L 9/01 422/122 |
| 8,602,765 B2* | 12/2013 | Jiang | ................ | B82Y 30/00 19/66 R |
| 8,846,144 B1* | 9/2014 | Wang | ................ | H01B 1/04 252/514 |
| 2004/0131811 A1* | 7/2004 | Lee | ................ | B01J 19/088 428/36.9 |
| 2008/0170982 A1* | 7/2008 | Zhang | ................ | B82Y 10/00 423/447.3 |
| 2008/0299031 A1* | 12/2008 | Liu | ................ | B82Y 30/00 423/447.3 |
| 2009/0110897 A1* | 4/2009 | Humfeld | ................ | B32B 7/14 428/221 |
| 2010/0224072 A1* | 9/2010 | Ulanov | ................ | A61L 9/12 96/222 |

* cited by examiner

*Primary Examiner* — Robet Clemenete
(74) *Attorney, Agent, or Firm* — Steven Reiss

(57) ABSTRACT

An air purifier includes a shell, a wind turbine and an air filter layer. The shell includes at least one air inlet and at least one air outlet, and an air passage is defined between the at least one air inlet and the at least one air outlet. The wind turbine is located in the air passage. The air filter layer is located in the air passage and includes a filter screen. The air filter screen includes a carbon nanotube structure including a plurality of carbon nanotube films stacked and crossed with each other. The carbon nanotube structure includes a plurality of micropores. A diameter of the micropores is ranged from about 1 micrometer to about 2.5 micrometers.

10 Claims, 10 Drawing Sheets

AIR PURIFIER

CROSS-REFERENCE TO RELATED APPLICATIONS

This application claims all benefits accruing under 35 U.S.C. §119 from China Patent Application No. 201420392710.9, filed on Jul. 16, 2014, in the China Intellectual Property Office, the contents of which are hereby incorporated by reference.

BACKGROUND

1. Technical Field

The disclosure generally relates to air purifiers.

2. Description of Related Art

PM 2.5 is particles with notional diameter of less than 2.5 µm. Compared with large diameter particles, PM 2.5 has small particle size, large surface area, and high activity. PM 2.5 easily adsorbs toxic substances, such as heavy metals and microorganisms. Additionally, PM 2.5 can stay a long time in the air. Thus the air pollution is more serious with an increasing concentration of PM 2.5 in the air. Breathing PM 2.5 is very unhealthy.

Recently, air purifiers are usually used for indoor air purification. However, filter layers of conventional air purifiers mostly have large and uneven apertures, which influence the filtration efficiency for PM 2.5.

BRIEF DESCRIPTION OF THE DRAWINGS

Implementations of the present technology will now be described, by way of example only, with reference to the attached figures.

DETAILED DESCRIPTION

Figure 1:
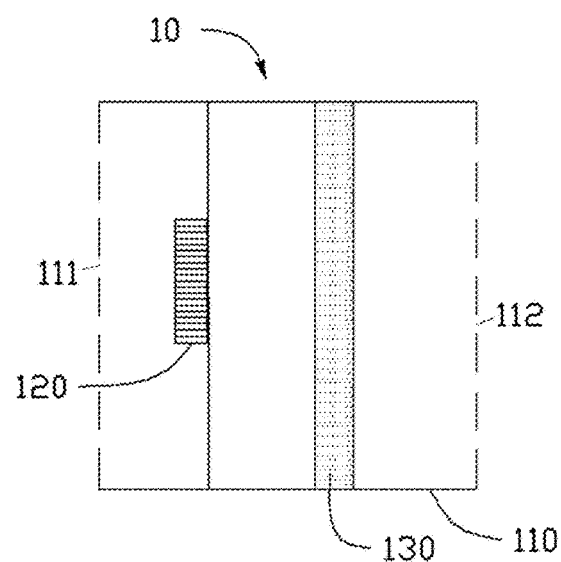
FIG. 1 is a sectional schematic view of one embodiment of an air purifier.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

Several definitions that apply throughout this disclosure will now be presented.

The term "substantially" is defined to be essentially conforming to the particular dimension, shape or other feature that the term modifies, such that the component need not be exact. For example, "substantially cylindrical" means that the object resembles a cylinder, but can have one or more deviations from a true cylinder. The term "comprising," when utilized, means "including, but not necessarily limited to"; it specifically indicates open-ended inclusion or membership in the so-described combination, group, series and the like. The expression "PM 2.5" can refer to particles of solid matter with a notional diameter of less than 2.5 µm or to a device to function against particles of such size.

Figure 2:
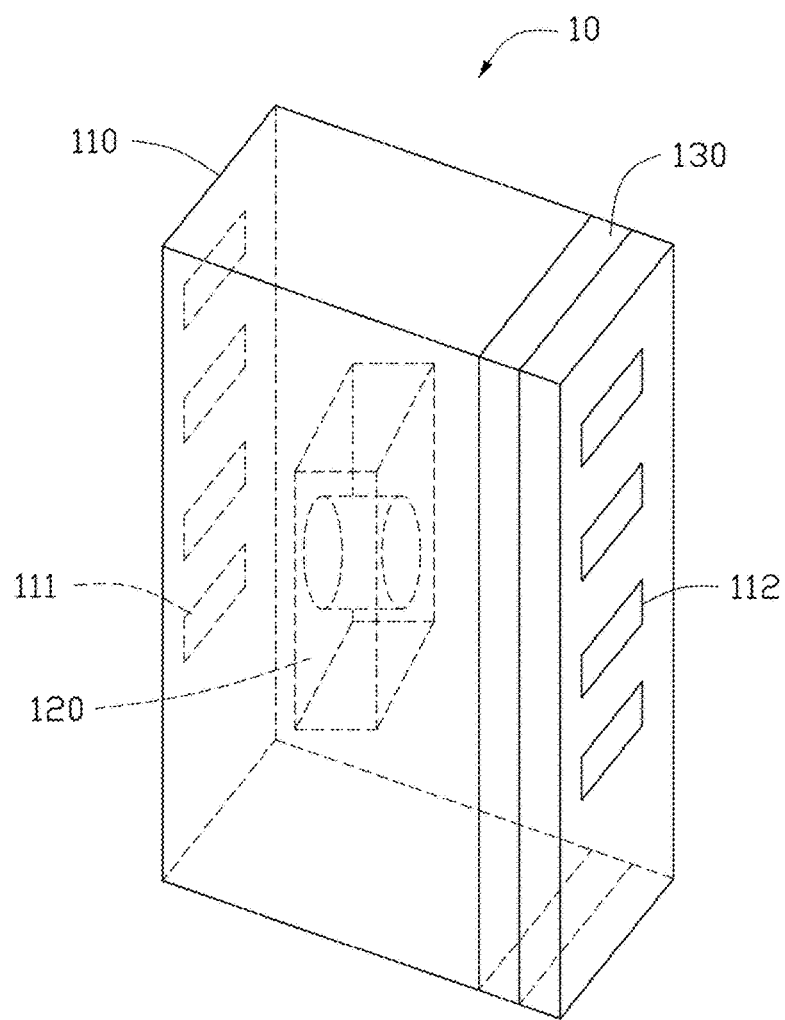
FIG. 2 is a three-dimensional schematic view of one embodiment of an air purifier.

FIGS. 1 and 2 illustrate one embodiment of an air purifier 10, which includes a shell 110, a wind turbine 120 and an air filter layer 130. The shell 110 includes at least one air inlet 111 and at least one air outlet 112. An air passage is defined between the air inlet 111 and the air outlet 112. The wind turbine 120 and the air filter layer 130 are located in the air passage.

A material of the shell 110 can be selected according to practice. In one embodiment, the material of the shell 110 is plastic. In another embodiment, the material of the shell 110 is metal. A shape and a size of the shell 110 can also be selected according to practice, in one embodiment, the shell 110 is rectangle.

A shape, a size and the number of the air inlet 111 and the air outlet 112 can be selected according to practice. In one embodiment, the air inlet 111 is connected with the air outlet 112 directly. In another embodiment, the air inlet 111 is connected with the air outlet 112 via a pipeline. The air inlet 111 and the air outlet 112 can be arranged as desired. In one embodiment, the air inlet 111 is located on a first surface of the shell 110, the air outlet 112 is located on a second surface opposed to the first surface.

The wind turbine 120 is used to continuously draw indoor air into the air purifier 10, and blow purified air out from the air outlet 112, thereby enabling indoor air flow cyclically.

Figure 3:
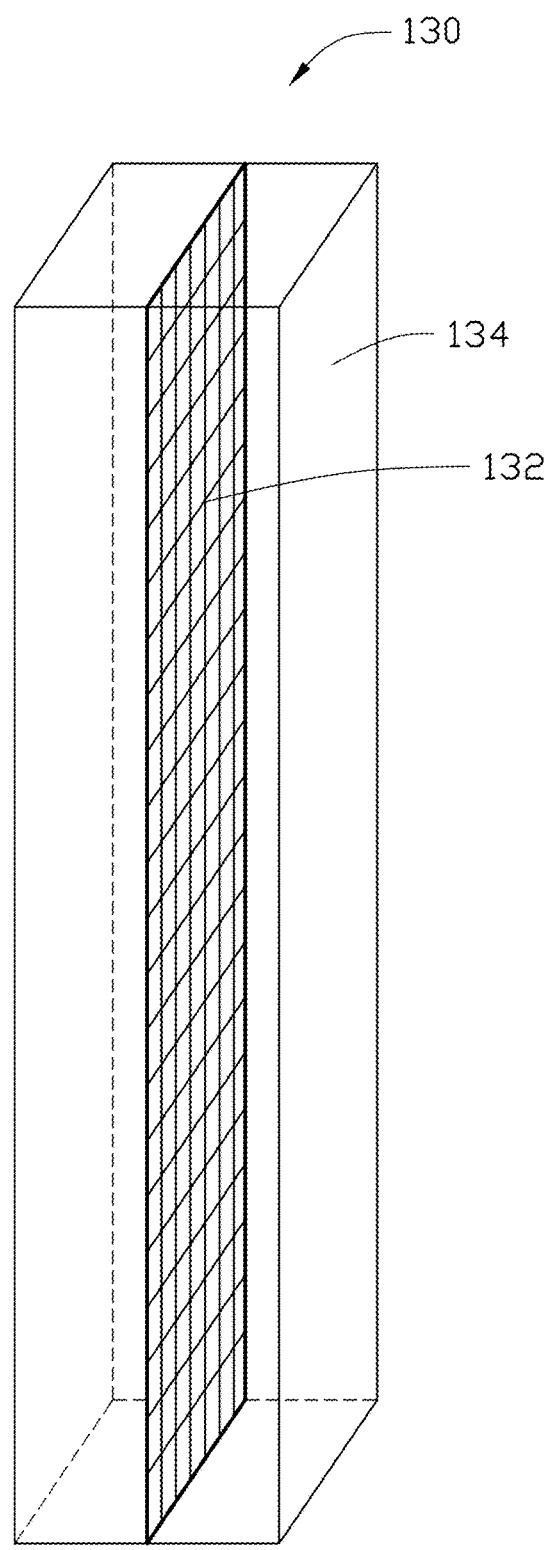
FIG. 3 is a schematic view of one embodiment of an air filter layer of an air purifier.
Figure 4:
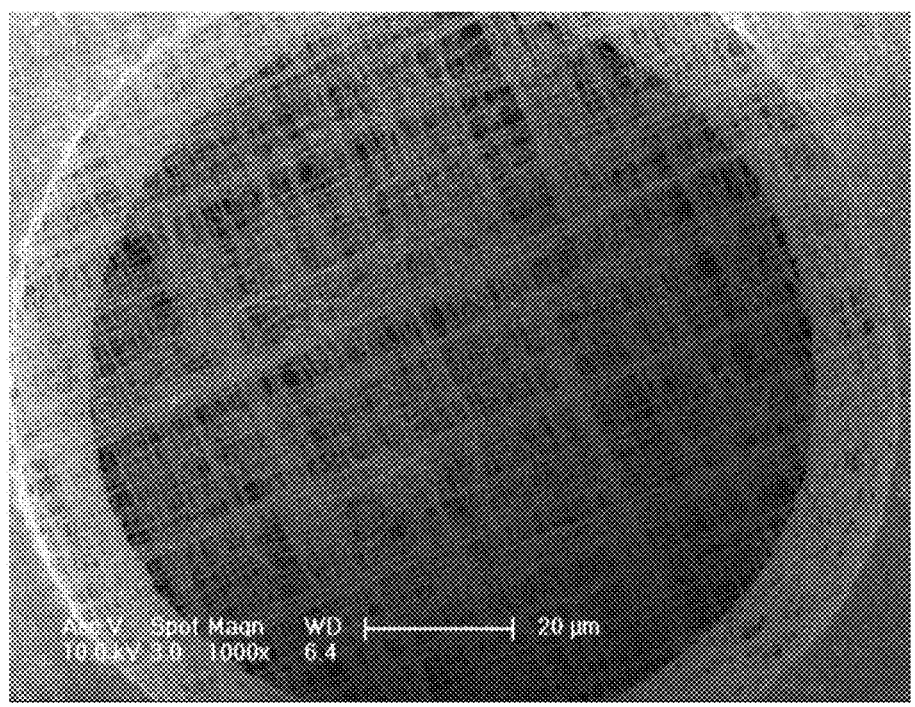
FIG. 4 is a scanning electron microscope (SEM) image of a carbon nanotube structure.
Figure 5:
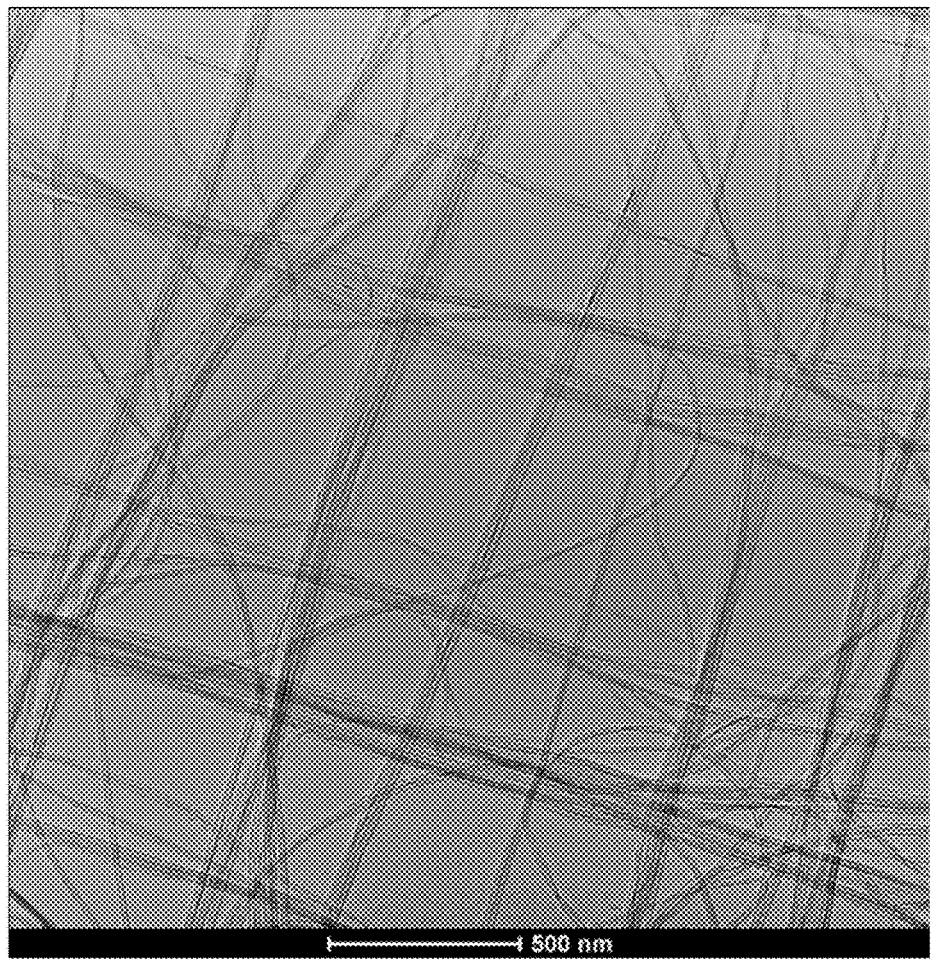
FIG. 5 is a transmission electron microscope (TEM) image of a carbon nanotube structure.

FIGS. 3-5 illustrate that the air filter layer 130 includes a filter screen 132. The filter screen 132 includes a carbon nanotube structure. The carbon nanotube structure includes a plurality of carbon nanotubes without impurities. In one embodiment, the filter screen 132 is substantially a pure carbon nanotube structure and consists essentially of just carbon nanotubes. The carbon nanotube structure includes a plurality of carbon nanotube films stacked and crossed with each other. The carbon nanotube structure includes a plurality of micropores. A diameter of the plurality of micropores is larger than 1 micrometer and less than 2.5 micrometers.

In one embodiment, the air filter layer 130 includes a frame 134 located in the air passage of the air purifier 10. The frame 134 can be removable. The filter screen 132 is located on the frame 134, and the frame 134 is used to support and fix the filter screen 132.

Each of the plurality of carbon nanotube films can be a drawn carbon nanotube film, a flocculated carbon nanotube film or a pressed carbon nanotube film.

Figure 6:
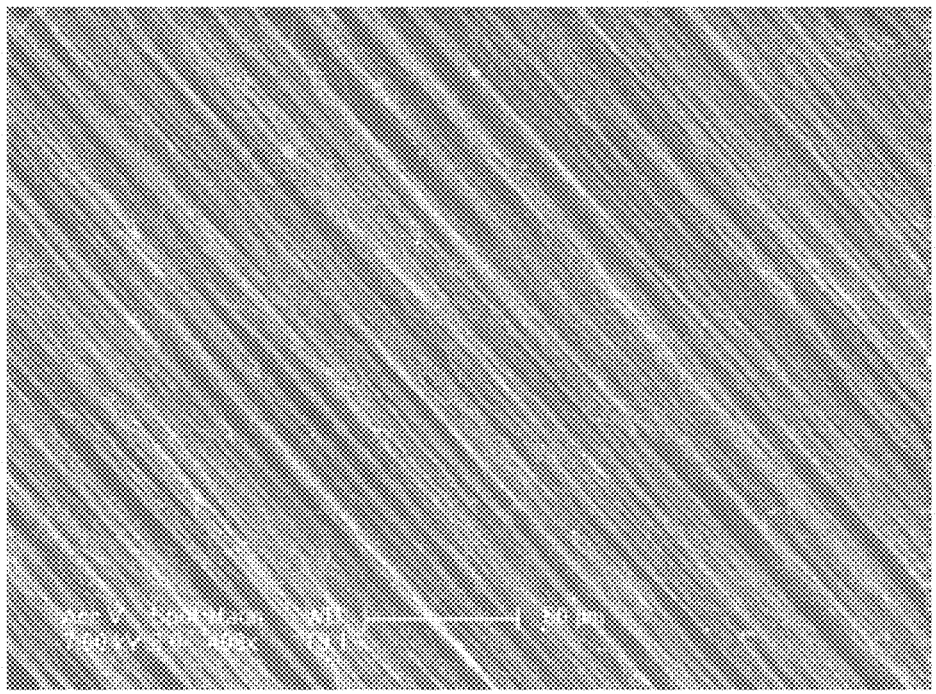
FIG. 6 is an SEM image of a drawn carbon nanotube film.

FIG. 6 illustrates that the drawn carbon nanotube film includes a number of carbon nanotubes that are arranged substantially parallel to a surface of the drawn carbon nanotube film. A large number of the carbon nanotubes in the drawn carbon nanotube film can be oriented along a preferred direction, meaning that a large number of the carbon nanotubes in the drawn carbon nanotube film are arranged substantially along the same direction. An end of one carbon nanotube is joined to an end of an adjacent carbon nanotube arranged substantially along the same direction, by van der Waals force, to form a free-standing film. The term 'free-standing' includes films that do not have to be supported by a substrate. The drawn carbon nanotube film can be formed by drawing from a carbon nanotube array. Examples of a drawn carbon nanotube film are taught by U.S. Pat. No. 7,045,108 to Jiang et al., and US patent application US 2008/0170982 to Zhang et al. A width of the drawn carbon nanotube film relates to the carbon nanotube array from which the drawn carbon nanotube film is drawn. A thickness of the carbon nanotube drawn film can range from about 0.5 nanometers to about 100 micrometers.

A minority of carbon nanotubes in the drawn carbon nanotube film may be randomly aligned. However, the number of randomly aligned carbon nanotubes is very small and does not affect the overall oriented alignment of the majority of carbon nanotubes in the drawn carbon nanotube film. The majority of the carbon nanotubes in the drawn carbon nanotube film substantially aligned along the same direction may not be exactly straight, and can be curved to a certain degree, or are not exactly aligned along the overall aligned direction, and can deviate from the overall aligned direction by a certain degree. Therefore, partial contacts can exist between the randomly aligned carbon nanotubes and adjacent carbon nanotubes. The drawn carbon nanotube film includes a plurality of successively oriented carbon nanotube segments joined end-to-end by van der Waals force. Each carbon nanotube segment includes a plurality of carbon nanotubes substantially parallel to each other, and combined together by van der Waals force.

Figure 7:
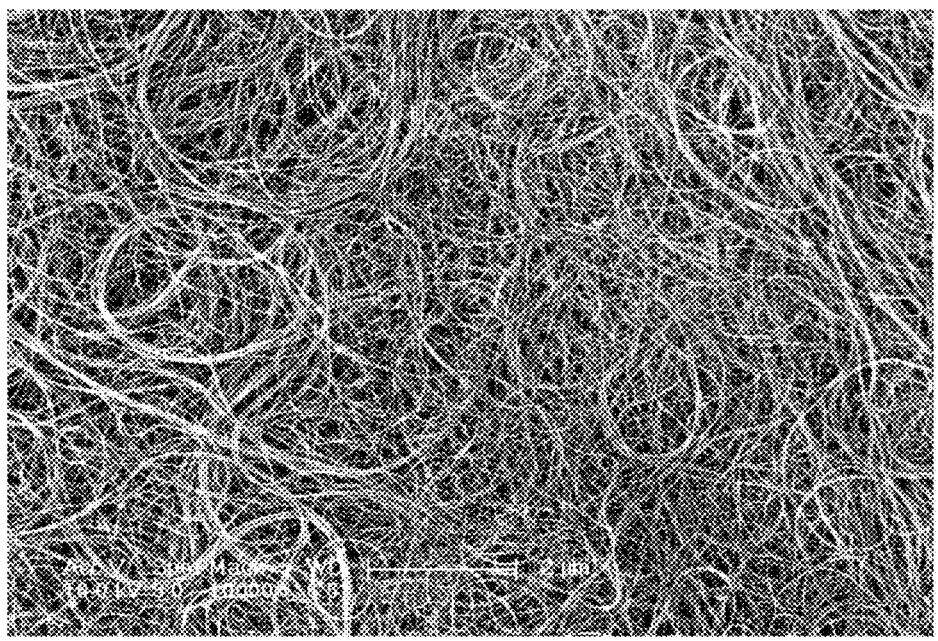
FIG. 7 is an SEM image of a flocculated carbon nanotube film.

FIG. 7 illustrates a flocculated carbon nanotube film which can include a number of carbon nanotubes entangled with each other. The carbon nanotubes can be substantially uniformly distributed in the flocculated carbon nanotube film. The flocculated carbon nanotube film can be formed by flocculating the carbon nanotube array. Examples of the flocculated carbon nanotube film are taught by U.S. Pat. No. 8,846,144 to Wang et al.

Figure 8:
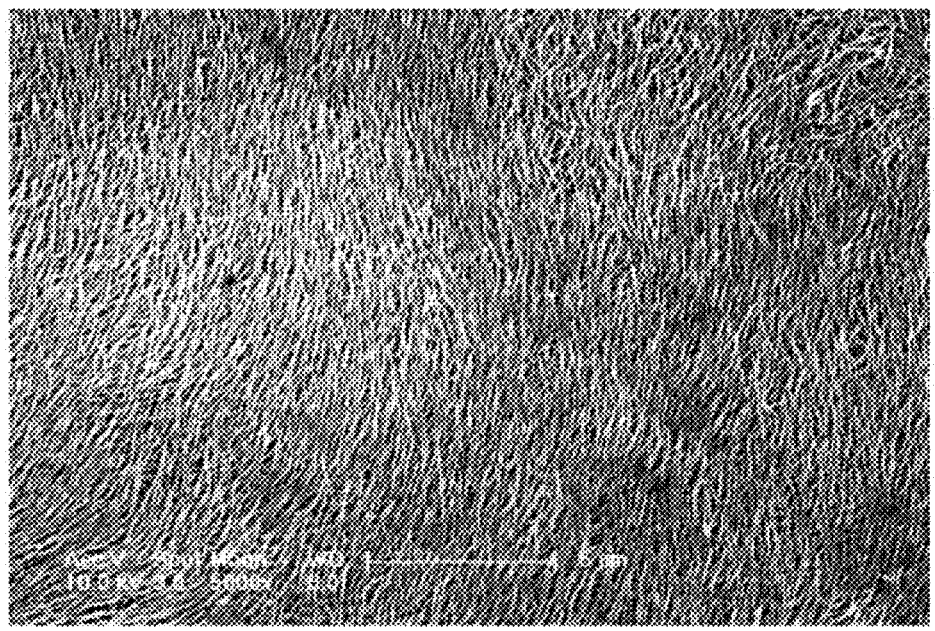
FIG. 8 is an SEM image of a pressed carbon nanotube film.

FIG. 8 illustrates a pressed carbon nanotube film which can include a number of disordered carbon nanotubes arranged along a same or different directions. Adjacent carbon nanotubes are attracted to each other and combined by van der Waals force. A planar pressure head can be used to press the carbon nanotubes array along a direction perpendicular to a substrate, thereby a pressed carbon nanotube film having a plurality of isotropically arranged carbon nanotubes can be obtained. A roller-shaped pressure head can be used to press the carbon nanotubes array along a fixed direction, thereby a pressed carbon nanotube film having a plurality of carbon nanotubes aligned along a fixed direction is obtained. The roller-shaped pressure head can also be used to press the array of carbon nanotubes along different directions, thereby a pressed carbon nanotube film having a plurality of carbon nanotubes aligned along different directions is obtained. Examples of pressed carbon nanotube films are taught by US PGPub. 20080299031A1 to Liu et al.

Adjacent carbon nanotube films of the plurality of stacked and crossed carbon nanotube films can be combined simply by van der Waals force. In some embodiments, the number of the plurality of carbon nanotube films is in a range from about four to about eight. When the number of carbon nanotube films is too small, the diameter of the plurality of micropores will be large, which is not appropriate for trapping PM 2.5. When the number of carbon nanotube films is too large, the breathability of the air purifier 10 will be reduced.

When a large number of the carbon nanotubes in each carbon nanotube film of the carbon nanotube structure is oriented along a preferred orientation, an angle between the aligned directions of the carbon nanotubes in two adjacent carbon nanotube films ranges from about 0 degrees to about 90 degrees.

In one embodiment, the carbon nanotube structure consists of four drawn carbon nanotube films stacked and crossed with each other, the angle between the aligned directions of the carbon nanotubes in adjacent drawn carbon nanotube films is about 90 degrees, and the diameter of the micropores is about 1.5 micrometers.

In one embodiment, the carbon nanotube structure includes a plurality of carbon nanotube wires. The carbon nanotube wires can be parallel to each other, braided together, or twisted together to form a carbon nanotube film. In one embodiment, the plurality of carbon nanotube wires are arranged along a same direction, a gap being defined between adjacent carbon nanotube wires.

The carbon nanotube wire can be an untwisted carbon nanotube wire or a twisted carbon nanotube wire.

Figure 9:
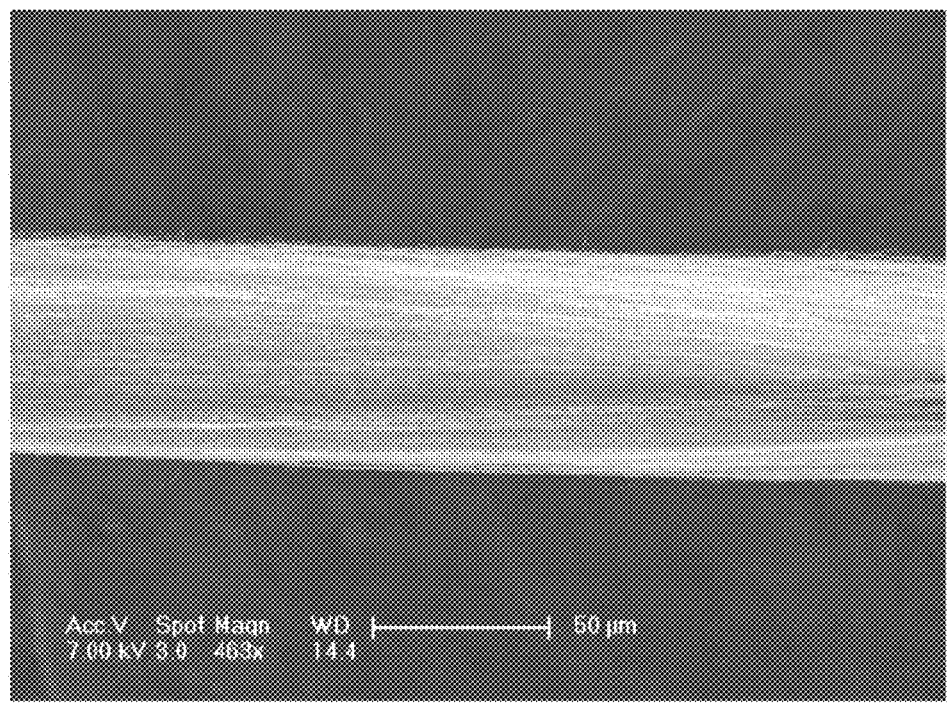
FIG. 9 is an SEM image of an untwisted carbon nanotube wire.

FIG. 9 illustrates that the untwisted carbon nanotube wire includes a plurality of carbon nanotubes substantially oriented along a length of the untwisted carbon nanotube wire. The untwisted carbon nanotube wire can be formed by treating a drawn carbon nanotube film with a volatile organic solvent. The drawn carbon nanotube film can be formed by drawing a film from a carbon nanotube array; the drawn carbon nanotube film being a free-standing structure. The drawn carbon nanotube film includes a plurality of carbon nanotube segments joined end-to-end by van der Waals force. Each carbon nanotube segment includes a plurality of carbon nanotubes substantially parallel to each other, and combined by van der Waals force. A length of the untwisted carbon nanotube wire can be set as desired. A diameter of the untwisted carbon nanotube wire can range from about 0.5 nanometers to about 100 micrometers. The drawn carbon nanotube film is treated by applying an organic solvent to the drawn carbon nanotube film so as to soak the entire surface of the drawn carbon nanotube film. After being soaked by the organic solvent, adjacent parallel carbon nanotubes in the drawn carbon nanotube film will bundle together when the organic solvent volatilizes, due to the surface tension of the organic solvent, thus the drawn carbon nanotube film will shrink into the untwisted carbon nanotube wire. The organic solvent can be volatile organic solvents, such as ethanol, methanol, acetone, dichloroethane, or chloroform. Compared with the drawn carbon nanotube film, a specific surface area of the untwisted carbon nanotube wire is decreased, and a viscosity of the untwisted carbon nanotube wire is increased.

Figure 10:
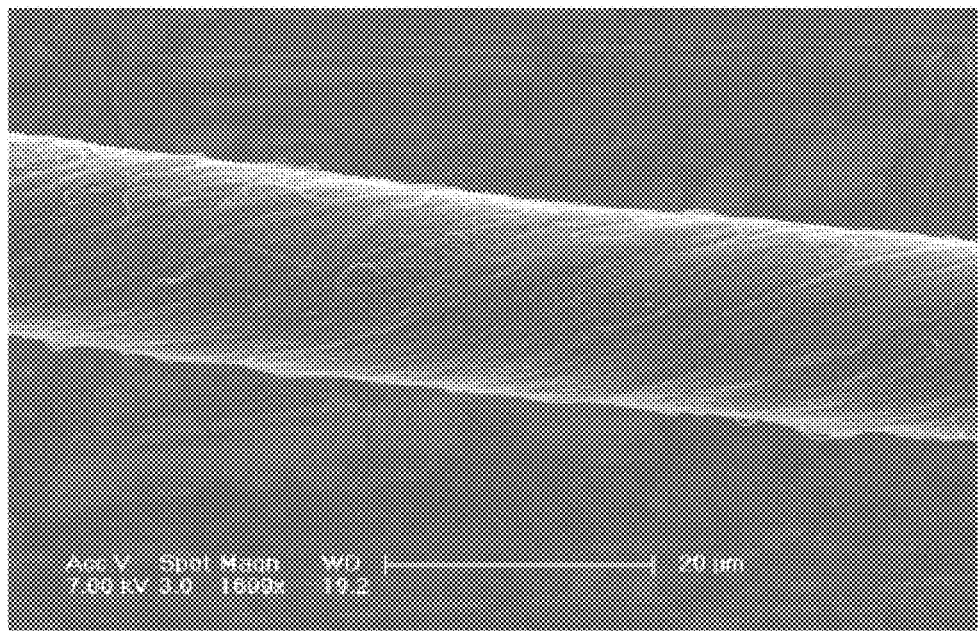
FIG. 10 is an SEM image of a twisted carbon nanotube wire.

FIG. 10 illustrates that the twisted carbon nanotube wire includes a plurality of carbon nanotubes spirally arranged along an axial direction of the twisted carbon nanotube wire. The twisted carbon nanotube wire is formed by twisting a carbon nanotube film. In one embodiment, the twisted carbon nanotube wire is treated by applying an organic solvent to the carbon nanotube film. After being soaked by the organic solvent, adjacent parallel carbon nanotubes in the carbon nanotube wire will bundle together as the organic solvent volatilizes, due to the surface tension of the organic solvent. A specific surface area of the twisted carbon nanotube wire is decreased, and a viscosity of the twisted carbon nanotube wire is increased.

Examples of the carbon nanotube wires are taught by U.S. Pat. No. 7,045,108 to Jiang et al., and U.S. Pat. No. 8,602,765 to Jiang et al.

The working principle of the air purifier 10 is as follows: indoor air is continuously absorbed into the air passage by the wind turbine 120, the indoor air is filtered by the air filter layer 130 to obtain purified air, and then the purified air is blown out from the air outlet 112.

The air purifier 10 can further includes a humidifying device (not shown). The humidifying device is used to increase air humidity. The humidifying device can be located at the air outlet 112.

The air purifier 10 can further includes a negative ion generator (not shown) located at the air outlet 112. When the air purifier 10 is in an operation, a negative high voltage is produced by the negative ion generator. The negative high voltage can ionize the air to obtain a large amount of negative ions. The negative ions and air pollution particles can agglomerate together, to make the air pollution particles sink, thereby further purifying the air. The negative ions can also deoxygenize reactive oxygen species produced by air pollutants, nitrogen oxides, cigarettes and so on, thereby reducing harm to human body caused by the reactive oxygen species. Additionally, a strong electric field generated by the negative ion generator can break through cell walls of some bacteria, viruses and microorganisms, to kill the bacteria, viruses and microorganism.

The air purifier 10 can further includes an intelligent monitoring system (not shown). The intelligent monitoring system is used to judge air quality in real time, monitor a life of the air filter layer 130 and a water level of a water tank, etc.

The humidifying device, the negative ion generator and the intelligent monitoring system are all optional elements. In some embodiments, the air purifier 10 does not include the humidifying device, the negative ion generator and the intelligent monitoring system.

The air purifier 10 includes a carbon nanotube structure. When the carbon nanotube structure includes four to eight carbon nanotube films stacked and crossed with each other, the diameter of the micropores in the carbon nanotube structure is larger than 1 micrometer and less than 2.5 micrometers. The air purifier 10 has excellent breathability, light weight and low cost.

The air filter layer 130 is formed by a plurality of stacked and crossed drawn carbon nanotube films, and a large number of the carbon nanotubes in each drawn carbon nanotube film oriented along a preferred orientation. Thus the plurality of micropores of the air filter layer 130 is uniform, which is appropriate for holding up PM 2.5.

A specific surface area of the carbon nanotubes is about 170 $m^2/g$, the carbon nanotube structure can filter out toxic gases from the air, thus the air purifier 10 can purify air without additional adsorption layers.

The carbon nanotubes have low specific surface area, and are combined by van der Waals force. Thus, the carbon nanotube structure has viscosity and can be adhered directly on the mask body 10 without an adhesive. Additionally, the carbon nanotube structure can uses this property of adherence to adhere to impurities which are difficult to filter.

It is to be understood that the above-described embodiments are intended to illustrate rather than limit the present disclosure. Variations may be made to the embodiments without departing from the spirit of the present disclosure as claimed. Elements associated with any of the above embodiments are envisioned to be associated with any other embodiments. The above-described embodiments illustrate the scope of the present disclosure but do not restrict the scope of the present disclosure.

What is claimed is:

1. An air purifier comprising:
    a shell comprising at least one air inlet and at least one air outlet, wherein an air passage is defined between the at least one air inlet and the at least one air outlet;
    a wind turbine located in the air passage; and
    an air filter layer located in the air passage and comprising a filter screen,
    wherein the air filter screen comprises a carbon nanotube structure comprising a plurality of carbon nanotube films stacked and crossed with each other; each of the plurality of carbon nanotube films comprises a plurality of carbon nanotube wires, and the plurality of carbon nanotube wires are braided or twisted together; and the carbon nanotube structure comprises a plurality of micropores, a diameter of the plurality of micropores is ranged from about 1 micrometer to about 2.5 micrometers.

2. The air purifier of claim 1, wherein each of the plurality of carbon nanotube films is selected from the group consisting of a drawn carbon nanotube film, a flocculated carbon nanotube film, and a pressed carbon nanotube film.

3. The air purifier of claim 1, wherein the carbon nanotube structure comprises four to eight drawn carbon nanotube films stacked and crossed with each other.

4. The air purifier of claim 3, wherein an angle between an aligned directions of carbon nanotubes in adjacent drawn carbon nanotube films ranges from about 0 degrees to about 90 degrees.

5. The air purifier of claim 4, wherein the carbon nanotube structure comprises four drawn carbon nanotube films stacked and crossed with each other, the angle between the aligned directions of the carbon nanotubes in adjacent drawn carbon nanotube films is about 90 degrees.

6. The air purifier of claim 1, wherein the diameter of the plurality of micropores is about 1.5 micrometers.

7. The air purifier of claim 1, further comprising a removable frame, and the filter screen is located on the removable frame.

8. The air purifier of claim 7, wherein the carbon nanotube structure has viscosity, and the filter screen adhered directly on the frame without an adhesive.

9. The air purifier of claim 1, further comprising a humidifying device located at the air outlet.

10. The air purifier of claim 1, further comprising a negative ion generator located at the air outlet.

* * * * *